US012614901B2

(12) United States Patent
Gross

(10) Patent No.: US 12,614,901 B2
(45) Date of Patent: Apr. 28, 2026

(54) CABLE ROUTING FOR A COMPUTED TOMOGRAPHY SYSTEM

(71) Applicant: Siemens Healthineers AG, Forchheim (DE)

(72) Inventor: Stefan Gross, Trabitz (DE)

(73) Assignee: SIEMENS HEALTHINEERS AG, Forchheim (DE)

(*) Notice: Subject to any disclaimer, the term of this patent is extended or adjusted under 35 U.S.C. 154(b) by 17 days.

(21) Appl. No.: 18/359,130

(22) Filed: Jul. 26, 2023

(65) Prior Publication Data

US 2024/0032883 A1 Feb. 1, 2024

(30) Foreign Application Priority Data

Jul. 29, 2022 (EP) .................................... 22187855

(51) Int. Cl.
| | |
|---|---|
| *H02G 11/00* | (2006.01) |
| *A61B 6/00* | (2006.01) |
| *A61B 6/03* | (2006.01) |
| *H02G 3/04* | (2006.01) |

(52) U.S. Cl.
CPC ............. *H02G 11/00* (2013.01); *A61B 6/032* (2013.01); *A61B 6/035* (2013.01); *A61B 6/4405* (2013.01); *A61B 6/4435* (2013.01); *A61B 6/4464* (2013.01); *A61B 6/56* (2013.01); *H02G 3/0456* (2013.01)

(58) Field of Classification Search
CPC ..... A61B 6/4464; A61B 6/4405; A61B 6/035; A61B 6/56; H02G 11/00
See application file for complete search history.

(56) References Cited

U.S. PATENT DOCUMENTS

| | | | | |
|---|---|---|---|---|
| 2,997,585 A | * | 8/1961 | Schiring .............. | A61B 6/4464 |
| | | | | 378/189 |
| 4,879,737 A | * | 11/1989 | Grady ...................... | A61B 6/00 |
| | | | | 378/195 |
| 5,327,474 A | * | 7/1994 | Inoue ..................... | A61B 6/032 |
| | | | | 378/116 |
| 5,410,767 A | | 5/1995 | Barud | |

(Continued)

FOREIGN PATENT DOCUMENTS

| | | |
|---|---|---|
| CN | 113086758 A | 7/2021 |
| CN | 215710737 U | 2/2022 |

(Continued)

*Primary Examiner* — Bradley Duckworth
(74) *Attorney, Agent, or Firm* — Harness, Dickey & Pierce, P.L.C.

(57) ABSTRACT

A cable routing system for a computed tomography system having a gantry configured to be adjusted in a movement direction extending perpendicular to the gantry, the cable routing system comprising: a vertical column arranged on the gantry and extending vertically from a base of the computed tomography system; and a first and a second articulated arm. The first articulated arm is rotatably attached to an upper end of the vertical column above the gantry via a first point of articulation. The first articulated arm is also rotatably attached to the second articulated arm, which is also arranged above the gantry, via a second point of articulation. The vertical column and the first and the second articulated arm are configured to route at least one supply line at least in part along their respective longitudinal axes.

20 Claims, 6 Drawing Sheets

(56)　　References Cited

U.S. PATENT DOCUMENTS

| | | | | | |
|---|---|---|---|---|---|
| 5,448,607 | A | * | 9/1995 | McKenna | A61B 6/035 |
| | | | | | 378/198 |
| 5,490,652 | A | * | 2/1996 | Martin | F16M 13/027 |
| | | | | | 248/282.1 |
| 5,521,957 | A | * | 5/1996 | Hansen | A61B 6/4441 |
| | | | | | 378/197 |
| 5,901,200 | A | * | 5/1999 | Krause | A61B 6/4464 |
| | | | | | 378/197 |
| 6,431,751 | B1 | | 8/2002 | Everett et al. | |
| 7,018,097 | B2 | * | 3/2006 | Schmitt | A61B 6/4452 |
| | | | | | 378/197 |
| 8,967,573 | B2 | * | 3/2015 | Hemmer | F16G 13/16 |
| | | | | | 248/323 |
| 9,523,463 | B2 | * | 12/2016 | Abri | F16M 11/425 |
| 11,279,246 | B2 | * | 3/2022 | Shin | B60L 53/35 |
| 11,963,809 | B2 | * | 4/2024 | Van Pinxteren | A61B 6/4464 |
| 2009/0154652 | A1 | | 6/2009 | Yi | |
| 2017/0360387 | A1 | * | 12/2017 | Gregerson | A61B 6/4405 |
| 2018/0312377 | A1 | | 11/2018 | Jakober et al. | |
| 2019/0090830 | A1 | | 3/2019 | Gao | |
| 2021/0308878 | A1 | | 10/2021 | Yoo et al. | |
| 2023/0355194 | A1 | | 11/2023 | Gregerson et al. | |
| 2024/0039266 | A1 | | 2/2024 | Gross et al. | |

FOREIGN PATENT DOCUMENTS

| | | | |
|---|---|---|---|
| DE | 102008035196 | A1 | 2/2010 |
| DE | 102018219541 | A1 | 5/2020 |
| DE | 102021202983 | A1 | 4/2022 |
| JP | H09220223 | A | 8/1997 |

* cited by examiner

CABLE ROUTING FOR A COMPUTED TOMOGRAPHY SYSTEM

CROSS-REFERENCE TO RELATED APPLICATION(S)

The present application claims priority under 35 U.S.C. § 119 to European Patent Application No. 22187855.6, filed Jul. 29, 2022, the entire contents of which are incorporated herein by reference.

FIELD

One or more example embodiments of the present invention provide a cable routing system for a movable computed tomography system, which is at least in part ceiling routed or extends above the gantry of the computed tomography system. Furthermore, one or more example embodiments of the present invention provide a computed tomography system having such a cable routing system is described.

BACKGROUND

In modern medical examination and treatment facilities, movable computed tomography (CT) systems are increasingly used. The movability of the systems predominantly serves the purpose of adjusting the typical sizes and space that CT systems take up in order to provide space in the immediate vicinity of the patient for medical personnel and/or further systems or devices that are used during an examination, a treatment and/or intervention. In this case, the focus is on the well-being and safety of the patient but also of the operating personnel and the machines.

In addition, a movability of the CT systems also offers the possibility of being able to move the CT systems into various treatment rooms and thus to reduce long term investment and maintenance costs.

It is known to adjust CT systems along rails so that the CT systems can assume predefined positions along the rails. Alternatively, freely movable CT systems are also available on the market. While freely movable CT systems comprise a rechargeable on-board energy supply, for example in the form of a lithium-ion memory, in the case of rail-borne systems the challenge is to realize the power supply in a wired manner.

In the case of CT systems that are used in different, typically two, treatment rooms, it is necessary for cable routing systems to be designed in a movable and flexible manner and namely so that they can bridge distances of up to 12 m. However, the mechanical strain cannot impair the serviceable life of the cable routing system.

Moreover, it is necessary to ensure that the cable routing system itself in the case of an adjustment movement of the CT system must not cause collisions with the patient, medical personnel or surrounding devices.

Accordingly in the prior art solutions are provided for cable routing that are arranged in the floor, typically near to the rail system. Collisions are to a large extent ruled out here. However, these solutions require structural prerequisites of the hospital environment and are therefore not possible to implement without restriction. Moreover, the solutions are often not adapted to the hygiene requirements of a medical environment and are expensive.

Alternatively, solutions are known in which supply lines are arranged in a ceiling box via one or multiple cable carriers. The rail system extends here parallel to the longitudinal axis of the ceiling box. A vertical column is provided on the gantry and said vertical column moves with the gantry and the supply lines are routed through the column down to the base of the gantry where they are connected there. The length of the ceiling box in this case defines the maximum adjustment path for the gantry.

SUMMARY

Accordingly, an object of one or more embodiments of the present invention is to provide alternative mechanism and/or means for a cable routing for a movable CT system that render possible an increased movement flexibility in the case of a long serviceable life and low construction costs. In particular, an object of one or more embodiments of the present invention is to increase the movement freedom of wired and rail-borne CT systems to such an extent that they can be used in different treatment rooms with opposing operations.

At least this object is achieved by a cable routing system for a computed tomography system in accordance with the independent claim(s) and also a computed tomography system comprising the cable routing system in accordance with the coordinate claim.

The cable routing system in accordance with a first aspect of embodiments of the present invention serves the supply, in particular the energy supply of a computed tomography system. Accordingly, a supply line is an electrical cable. Alternatively or in addition thereto, the supply line serves the data communication of or to the computed tomography system. Data is present for example in the form of raw data or already reconstructed image data. Data can also comprise control data relating to the operation of the computed tomography system. In this respect, the supply line can also be designed as a data cable. The gantry of the computed tomography system is designed as adjustable and namely in a movement direction that extends perpendicular to the gantry. The gantry has a central opening, the bore, in which a patient can be at least in part positioned for an imaging. The patient longitudinal axis corresponds, in accordance with embodiments of the present invention, to the movement direction of the gantry.

In this respect, a human is assumed below as the patient without limitation of the generality. Fundamentally, the patient can also be an animal.

The cable routing system comprises in accordance with the first aspect of the present invention a vertical column that is arranged on the gantry and extends vertically from a base of the computed tomography system. The vertical column ends on the floor side on or with the base of the gantry and is consequently moved with the gantry if this gantry is displaced in the movement direction. The vertical column has a height that is greater than the height of the gantry including the base. The vertical column therefore protrudes above the gantry in terms of height. The vertical column is dimensioned so that it can receive or can route at least one supply line, preferably a plurality of supply lines, in itself. The vertical column in embodiments is made from aluminum sheet or from a plastic.

The cable routing system further comprises a first articulated arm and also a second articulated arm. The first articulated arm is rotatably attached to the upper end, in other words the end oriented toward the ceiling, of the vertical column above the gantry via a first point of articulation. In other words, the first articulated arm can change its relative position with respect to the gantry via a rotation or via a pivoting about the first point of articulation. The first articulated arm is furthermore rotatably attached to the second articulated arm, which is likewise arranged above the gantry, via a second point of articulation. In other words, the first articulated arm can also change its relative position to the second articulated arm via a rotation or via a pivoting about the second point of articulation.

Both the vertical columns as well as the first and the second articulated arm are designed so as to route at least one supply line, preferably a plurality of supply lines, which are then arranged parallel to one another or adjacent to one another, at least in part along their respective longitudinal axes. As already explained in the introduction with reference to the vertical column, the individual components of the cable routing system in each case form hollow spaces or inner regions that are at least in part shielded from the outside, which extend in each case in the longitudinal direction of the components and in which the at least one supply line can be received. The movement of the gantry of the CT system is decoupled from the second articulated arm by the first and the second point of articulation and also the first articulated arm, which causes a greater flexibility with regard to the ability to position the gantry.

In a preferred embodiment of the cable routing system, the second articulated arm is further rotatably attached via a ceiling-mounted third point of articulation above the gantry. The third point of articulation is consequently arranged near or on a ceiling of an examination or treatment environment. The third point of articulation can be positioned in embodiments in a fixed manner on the ceiling. In alternative embodiments, the position of the third point of articulation is designed as adjustable, preferably adjustable in a direction parallel to the movement direction of the gantry, as is further explained more precisely below.

The second articulated arm is therefore rotatably attached directly or indirectly to the room ceiling via the third point of articulation. In other words, the second articulated arm can change its relative position with respect to the room ceiling via a rotation or via a pivoting about the third point of articulation.

It is possible due to the provision of a third point of articulation on the second articulated arm to further increase the positioning freedom for the CT gantry. The movement of the gantry is decoupled from the ceiling to a maximum extent via the first and the second articulated arm that can be pivoted in each case against one another and against the gantry or the room ceiling. In particular, this decoupling renders possible a rotation of the gantry about a vertical axis that extends through the isocenter of the gantry.

The two articulated arms are produced in embodiments of the present invention on steel sheet, wherein the production process comprises in particular a lasering and bending. It is however not necessary to limit the production to these two steps. The articulated arms are thus comparatively cost-effective in production and have a low weight, which reduces the requirements of the design of the drive units.

The at least one supply line is routed in embodiments of the present invention in the vertical column and on the first, second and/or third point of articulation in a cable carrier. The cable carrier forms an additional mechanical protection for the at least one supply line. In particular, the at least one supply line extends on the points of articulation at least in sections outside of the components of the cable routing system. In particular, on the points of articulation sections of the at least one supply line are provided that at least in some relative positions of the articulated arms or with respect to one another or with respect to the gantry or room ceiling in each case form a so-called reserve loop. In order to protect this reserve loop, a cable carrier is attached to the at least one supply line at the mentioned positions. This prevents for example damage to the supply line due to impact or collision, however also prevents an excess bending or buckling of the supply line, which leads to damage.

In embodiments of the cable routing system, the first and the second articulated arm extend or lie or move in one plane. This means that the first, the second and the third point of articulation in each case render possible a rotation or a pivoting about rotation axes that are arranged parallel to one another. According to a preferred embodiment variant, the two articulated arms lie in a horizontal plane, in other words are arranged parallel with respect to a floor or the room ceiling. The points of articulation can accordingly be designed in a particularly simple manner since they must in each case only provide one movement degree of freedom for the pivoting movement.

The vertical column can however also be designed in a height adjustable manner. Then in embodiments, the first, second and/or third point of articulation can be designed to also render possible a pivoting movement about a horizontal axis. In this case, the height of the vertical column, in particular subsequently, in other words after installing the CT system can be easily adapted in order to maintain for example spatial specifications of a specific treatment environment. In other embodiments, the height of the vertical column is already set prior to an assembly, for example at a predominant room height. It is then sufficient that first, second and/or third point of articulation have in each case only one degree of freedom. The ability to adjust the height of the vertical column can be realized for example via a telescoping embodiment. In this case, the vertical column comprises for example two or more hollow profile segments of which in each case two are at least in part guided in one another. It is possible due to extending the individual profile segments from the in each case supporting segment to subsequently achieve an elongation of the vertical column. A shortening can be achieved accordingly in reverse by retracting the profile segments into one another.

The ability to adjust the height of the vertical columns serves primarily to adapt the cable routing system to existing spatial specifications, in particular a room ceiling height, in other words a compensation between the height of the third point of articulation and the vertical column height.

The second point of articulation of the cable routing system, in accordance with embodiments of the present invention, is preferably designed in such a manner that it renders possible positions in which the first articulated arm and the second articulated arm include an angle between 10° and 170°. The angle specification relates in this case to the two longitudinal axes of the articulated arms. In other words, the second point of articulation renders possible orientations of the first and second articulated arm in which these are arranged almost or essentially parallel either one behind the other or one adjacent to the other. The first orientation renders possible an advantageously large spacing between the vertical column and the third point of articulation that is hung from the ceiling, which increases the movement freedom for the gantry. The second mentioned orientation conversely realizes a minimal footprint of the entire CT system. In other words, the CT system with this orientation of the two articulated arms requires as little as possible floor space or space requirement. This advantageously renders possible a smaller dimensioning of parking areas for the CT system if this is not in operation.

In a further embodiment of the cable routing system in accordance with the present invention, the first point of articulation is designed in such a manner that it renders possible positions in which the first articulated arm and the gantry include an angle between 10° and 160°. The angle specification relates in this case to a zero position of the first articulated arm, which is defined beforehand. Via the rotational angular range of the first and of the second point of articulation, which is predetermined as particularly wide, the cable routing system renders possible in particular a rotation of the gantry about 180°.

In a further embodiment of the cable routing system, the third pivot point is also designed so that it renders possible positions in which the second articulated arm and an axis on the room ceiling that is to be defined beforehand include an angle between 10° and 160°. As a consequence, the movement freedom of the CT system is further increased since consequently also the second articulated arm can span a wide angular range starting from the third point of articulation.

The lengths of the first and the second articulated arm are selected, in accordance with embodiments of the present invention, so that the length of the first articulated arm corresponds to 65% to 75%, in particular 68% to 72%, particularly preferably 70% of the length of the second articulated arm. Empirically, the inventor has been able to establish that this length ratio of the articulated arms particularly effectively supports a movement freedom of the gantry. In particular, this length ratio of the articulated arms supports a purely rotational movement of the gantry about a vertical axis through its isocenter about 180°.

In a particularly preferred embodiment, the first articulated arm is maximum 1600 mm long and the second articulated arm is maximum 2300 mm long. With the indicated maximum lengths of the articulated arms it is possible using the previously described cable routing system to already achieve a maximum extension path for the gantry of 5600 mm. The lengths of the two articulated arms can also be shortened in embodiments corresponding to the above ratio in order to adapt the cable guiding system to structural circumstances of the examination environment or the dimensions of the CT system.

The cable routing system further comprises in a preferred embodiment a horizontal column that extends above the gantry, is ceiling-mounted and extends in its longitudinal axis parallel to the movement direction of the gantry. In this case, a carriage that can be adjusted in the longitudinal direction of the horizontal column is arranged on the horizontal column and the carriage supports the third point of articulation. The third point of articulation, which in the previous embodiments was fixedly positioned on the room ceiling, can adjust in this embodiment parallel to the movement direction of the gantry. Advantageously, the carriage in this case can adjust over essentially the entire length of the likewise ceiling-mounted horizontal column. In this manner, the maximum extension path of the gantry extends with the maximum lengths of the first and second articulated arm to 12 m and in this case comfortably renders possible a use of the computed tomography system in multiple treatment rooms.

Alternatively or in addition to a height adjustable vertical column, like that already described above, it is also possible for the carriage to be designed to adjust the height of the third point of articulation with the result that an adaptation of the cable routing system to a predetermined room ceiling height can also be realized via the carriage.

The at least one supply line is then guided further starting from the third point of articulation on the carriage at least in part in at least one, preferably two, cable carriers in the horizontal column. The cable carriers in each case ensure, as already described in the introduction, a mechanical protection of the at least one supply line and prevent in particular a bending of the supply line if the carriage is adjusted between a first end of the horizontal column and the second end of the horizontal column along its longitudinal axis.

In embodiments of the present invention, the carriage can be moved passively by a drive that is provided in the gantry or in the base of the gantry. In other embodiments, the carriage can alternatively or in addition comprise a dedicated drive unit in order to move the carriage actively along the horizontal column. This is in particular advantageous in order to bring the CT system into its park position or into its parking position in which the first and the second articulated arm assume an angle of 10° with respect to one another and are arranged essentially lying adjacent to one another.

The horizontal column in embodiments of the present invention has a length of maximum 7 m along the movement direction of the gantry. In other words, in the case of a movement of the gantry the carriage is adjusted over a path of maximum 7 m.

A further aspect relates to a computed tomography system for generating tomographic X-ray images. This comprises a gantry that can be adjusted in a movement direction that extends perpendicular to the gantry, and also a cable routing system in accordance with embodiments of the present invention that is designed as already described above. The computed tomography system is configured so as to generate tomographic image data of a patient, more precisely a body region of a patient via X-ray radiation. For this purpose, the computed tomography system in its gantry comprises imaging components in the form of at least one X-ray radiation source and at least one X-ray radiation detector that is arranged lying opposite. The X-ray radiation source is designed so as to generate X-ray radiation and to transmit in the direction of the patient who is arranged in the isocenter of the gantry. The X-ray radiation is attenuated by the tissue distribution of the examined or mapped body region and impinges on the X-ray detector after the X-ray radiation has penetrated the patient. The imaging components of the CT system are rotatably arranged in the gantry with the result that projection data can be generated from a plurality of different angular positions. The CT system further comprises a computing unit that is designed so as to reconstruct a preferably three-dimensional tomographic X-ray image of the body region from a plurality of projection data that is acquired.

In embodiments, the CT system can comprise a rail system that extends in the above-described movement direction of the gantry. The rail system can comprise in this case one, however also two or more rails. The rails are designed in a preferred embodiment as straight. In particular embodiments, the rail system extends over a length of up to 12 m. This maximum extension path extends particularly advantageously and over two examination spaces of a medical facility. At a maximum extension of 12 m, two spacious examination spaces can be used with only one CT system in that the gantry of the CT system is adjusted along the rail system. In this case, the above-described cable routing system, which is designed in embodiments, so as to carry the at least one supply line over this maximum extension path, provides support.

In an advantageous embodiment, a park position is provided between the two examination spaces that can be separated via, for example, sliding doors of the examination spaces in order to position the CT system there out of operation. This park position can be designed in a particularly advantageous embodiment as particularly small or narrow since the two articulated arms of the cable routing system can be positioned particularly close, almost in parallel to one another.

In a further embodiment, the horizontal column can comprise a roller conveyor cover on the longitudinal side on which the carriage is guided. The roller conveyor cover predominantly serves to close the horizontal column. The roller conveyor cover can be made for example from plastic. The roller conveyor cover can alternatively be designed as metal and in this manner reduces leakage radiation between the two examination spaces.

The CT system is moreover designed in the case of an adjustment movement along the rail system so as to perform a rotation of the gantry by a maximum of 180° about a vertical axis, which extends through the isocenter of the gantry. Alternatively, the gantry can also be rotated in a stationary position. In this case, again the cable routing system in accordance with embodiments of the present invention provides support. Via the specific length ratio between the first and the second articulated arm, the gantry can itself perform a rotation by 180° about the isocenter axis without a translational movement along the rail system.

In this case, the CT system can comprise a rotational drive or a rotary bearing that acts between the base of the CT system and gantry. In other words, the base can be designed so as to be oriented rigidly and so as to be fixedly connected to the rail system. The gantry conversely can be rotated by the rotary drive with respect to the base.

Example advantages of embodiments of the present invention are summarized again below:

The cable routing system renders possible a particularly long extension path for the gantry of a CT system and is suitable therefore particularly for use in two space environments.

In addition to the extension path, the cable routing system renders possible a 180° rotation of the gantry about the vertical axis through its isocenter. The rotation of the gantry improves the accessibility of the gantry in such a manner that the patient or a patient couch can be pushed together with the patient in any of the examination spaces of a two-space environment from the outside of the examination spaces into the gantry, which greatly simplifies the patient positioning and thus the examination procedure.

The cable routing system provides a simple accessibility to the at least one supply line, all lines or cables can be easily removed. This simplifies the maintenance of the system.

The cable routing system requires less space on the room ceiling with the result that free space is provided for other, in particular interventional imaging systems, for example a C-arm system having an adjustment direction that is transverse with respect to the movement direction of the gantry.

In addition, the cable routing system renders possible a sliding door between the two examination spaces both in the as well as outside of the operation of the CT system.

BRIEF DESCRIPTION OF THE DRAWINGS

The above-described characteristics, features and advantages of this invention and also the manner in which these are achieved become clearer and more easily understandable in conjunction with the following description of the exemplary embodiments that are further explained in conjunction with the drawings. The present invention is not limited to these exemplary embodiments on account of this description. In various figures, identical components are provided with identical reference characters. In general, the figures are not to scale. In the drawings.

DETAILED DESCRIPTION

Figure 1:
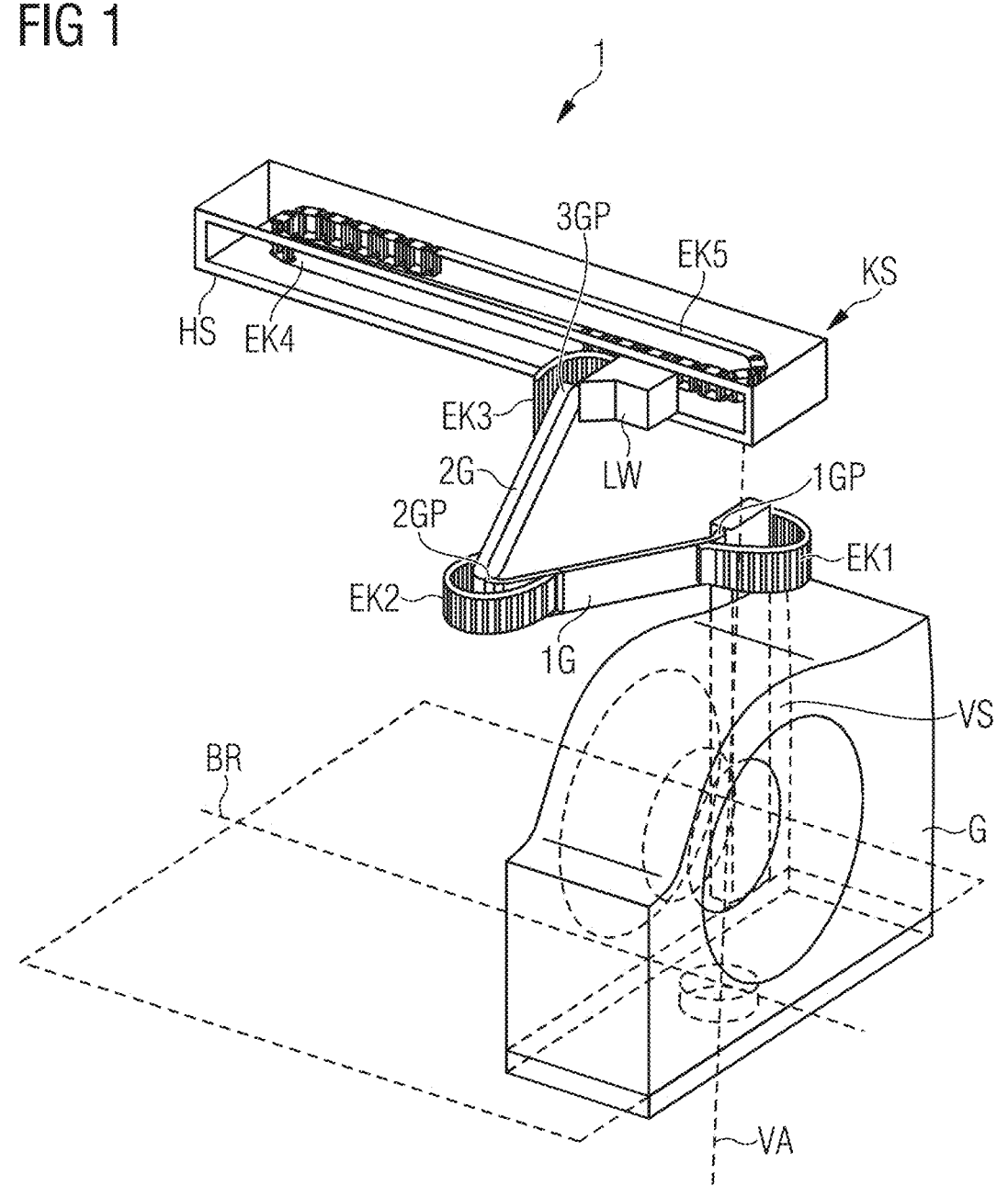
FIG. 1 shows a perspective view of a cable routing system in a first embodiment of the present invention.

FIG. 1 illustrates a perspective view of a cable routing system KS in a first embodiment of the present invention. The cable routing system KS is designed for a computed tomography system 1. This has a gantry G that can be adjusted or displaced along a movement direction BR that extends perpendicular with respect to the gantry G. The cable routing system KS comprises a vertical column VS that is arranged here at the side or the corner of the gantry G and extends vertically upward from a base of the computed tomography system 1. Moreover, a first articulated arm 1G and also a second articulated arm 2G is included. The first articulated arm 1G in this case is rotatably attached to an upper end of the vertical column VS above the gantry G via a first point of articulation 1GP and is also rotatably attached to the second articulated arm 2G, which is likewise arranged above the gantry G, via a second point of articulation 2GP. The first point of articulation 1GP therefore means that the first articulated arm 1G cannot just pivot above, but rather also at least in part via the gantry G. The second point of articulation 2GP means that a relative position between the first and second articulated arm 1G, 2G can be changed. The vertical column VS has a height that extends up to over the gantry G. The height of the vertical column VS is in this case designed so that a minimum spacing or safety spacing is maintained between the highest point of the gantry G and the underside of the first articulated arm 1G. The vertical column VS and also the first and second articulated arm 1G, 2G are in each case hollow spaces or designed as having inner lying regions with the result that they can route at least one, typically a plurality, of supply lines (not illustrated) in the form of electrical or data cables at least in part along their respective longitudinal axes. In other words, in each case at least part sections of the at least one supply line extend within the vertical column VS, the first articulated arm 1G and the second articulated arm 1G. The at least one supply line extends according to its length consequently over the entire length of the vertical column VS, first and second articulated arm 1G, 2G and is guided by the extent of the mentioned components of the cable routing system KS.

The second articulated arm 2G in this embodiment is furthermore rotatably attached via a ceiling-mounted third point of articulation 3GP above the gantry G. Ceiling-mounted means in this context that the third point of articulation 3GP is mounted or fastened close to the or on the ceiling. As a consequence, the second articulated arm 2G can also not just be pivoted or positioned above but rather at least also in part via the gantry G. The third point of articulation 3GP in this embodiment is arranged on a carriage LW. This is attached for its part to a horizontal column HS that is mounted above the gantry G and extends mounted on the ceiling in other words directly on the room ceiling. The horizontal column HS extends according to its longitudinal axis parallel to the movement direction BR of the gantry G. The carriage LW is arranged on a longitudinal side of the horizontal column HS so that the carriage can be adjusted along the length of the horizontal column. In this manner, the carriage LW and thus the third point of articulation 3GP can be moved over essentially the entire length of the horizontal column HS in the movement direction BR of the gantry G, which advantageously increases the movement freedom for the gantry G. The horizontal column HS in the present case has a length of 7 m. It can however also be embodied shorter, for example 6 m, 5 m or the like, depending on the structural requirement of the medical facility. In this embodiment of the present invention, the carriage comprises a drive (not illustrated) that actively displaces the carriage LW during an adjusting movement of the gantry G. In other embodiments, the displacement of the carriage can also be performed passively or by the drive of the gantry G.

In further embodiments that are not illustrated here, the third point of articulation 3GP is mounted fixedly on the room ceiling. That is, the third point of articulation cannot be moved. These embodiments are particularly well adapted for single room applications.

The carriage LW in the present case is designed so as to adjust the height of the third point of articulation 3GP. In other words, the carriage renders it possible to compensate between room ceiling height and height of the vertical column VS or the heights of the three points of articulation 1GP, 2GP, 3GP that always lie in a common plane, preferably in a horizontal plane, in other words parallel to the room ceiling or to the floor. For this purpose, the carriage LW comprises in this embodiment a for example telescopically designed adjusting mechanism (not illustrated) in order by vertical retraction or extension of at least one telescopic segment to set the height of the third point of articulation 3GP.

The at least one supply line in the present case has a part section that is further routed in a cable carrier or in multiple, preferably two, cable carriers EK4, EK5 in the horizontal column HS. The horizontal column HS as a further component of the cable routing system KS likewise ensures a routing of the at least one supply line.

The supply line is not only routed in the horizontal column HS but rather also in the vertical column VS in a cable carrier. Moreover, in the present case in each case cable carriers EK1, EK2, EK3, in which the supply line is routed are provided on or in the regions of the first, second and third point of articulation 1GP, 2GP, 3GP. The at least one supply line at these points does not extend in a protected hollow space or inner region of the routing components and must in particular be mechanically protected there. Moreover, the at least one supply line forms reserve loops, which must be specially secured, at the points of articulation 1GP, 2GP, 3GP in specific positions of the articulated arms 1G, 2G and the gantry G and of the carriage LW. Cable carriers in general ensure a stabilization of the at least one supply line, prevent damage or excess bending or twisting.

In addition to the carriage LW that can adapt the third point of articulation 3GP in its height, in the present case the vertical column VS is also designed as height-adjustable with the result that the first and second point of articulation 1GP, 2GP can also be adapted in their height in order to set a suitable operating plane for the points of articulation. In this sense, in the illustrated embodiment at least the first and the third point of articulation 1GP, 3GP is designed not only to render possible a pivoting movement about a vertical axis but rather also to render possible a pivoting movement about a horizontal axis. The vertical column VS can comprise a telescopic mechanism that is preferably arranged on the upper end of the vertical column VS that sets the height of the first point of articulation 1GP by retracting and extending at least one telescopic section.

The second point of articulation 2GP in the present case is designed in such a manner that it renders possible positions in which the first articulated arm and the second articulated arm 1G, 2G include an angle between 10° and 170°. The first and third point of articulation 1GP, 3GP can consequently be almost the maximum distance away from one another (corresponding to the sum of their individual lengths) or the minimum distance away from one another (corresponding to a difference of their individual lengths), which further increases the movement freedom for the gantry G.

The first point of articulation 1GP is further designed so that it renders possible positions in which the first articulated arm 1G and the gantry G include an angle between 10° and 160°. The same angular range likewise applies for the third point of articulation 3GP. The articulation system comprise the two articulated arms 1G, 2G and the three points of articulation 1GP, 2GP, 3GP render possible arbitrary positions between the gantry G and the third point of articulation 3GP. Due to the provision of the carriage LW or the horizontal column HS, the movement radius for the gantry G is advantageously further extended.

The length of the first articulated arm 1G corresponds in accordance with the present invention to 65% to 75%, here approximately 70% of the length of the second articulated arm 2G. Due to maintaining this length ratio, the gantry G can be rotated by 180° in a stationary manner about a vertical axis VA. In the present case, the dimensions of the gantry G and also the use of a computed tomography system 1 in a two-space environment require that the first articulated arm 1G is 1600 mm long and the second articulated arm 2G is 2300 mm long.

Without the horizontal column HS or carriage LW, the cable routing system KS having these articulated arm lengths renders possible a maximum extension path along the movement direction BR for the gantry G of 5600 mm, with 7 m longer horizontal column HS the maximum extension path increases to 12 m.

Figure 2:
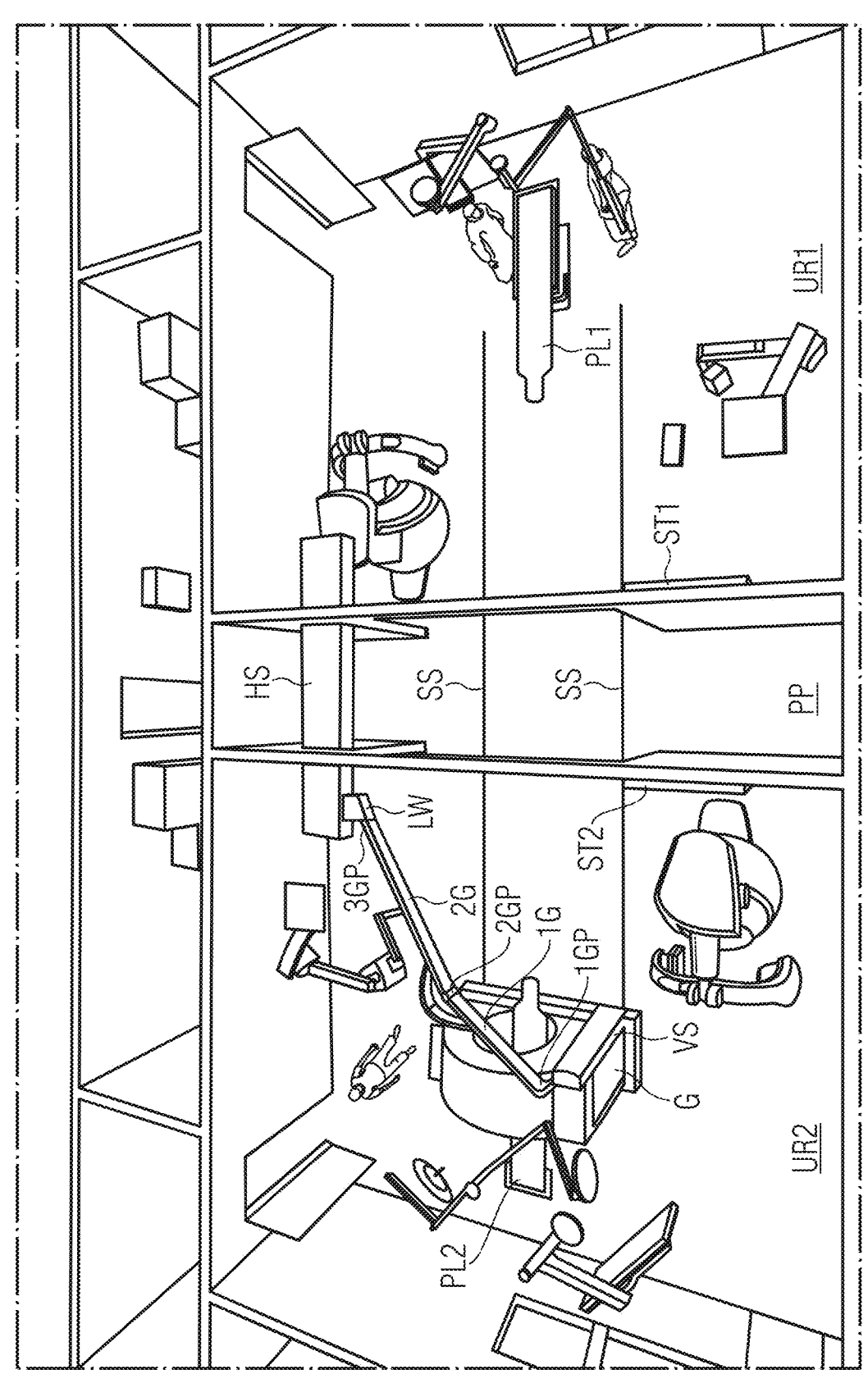
FIG. 2 shows a perspective view of a computed tomography system, which is arranged in an examination environment, together with the cable routing system in one embodiment of the present invention in a first operating position.

FIG. 2 illustrates a perspective view of a computed tomography (CT) system 1, which is arranged in an examination environment, together with the cable routing system KS in one embodiment of the present invention in a first operating position. The examination environment is a two-space environment comprising two examination spaces UR1 and UR2. These are spatially separated from one another by a park position PP. If the CT system 1 is not used or if it is not in operation, it can be brought into the park position PP and the examination spaces UR1, UR2 can be further used for other medical applications. For this purpose, in each case also further medical devices and systems, inter alia C-arms or monitors, are also provided in the examination spaces UR1, UR2 for the in-situ image display or devices for monitoring physiological functions of a patient. Furthermore, patient couches PL1, PL2 are arranged in each case in each examination space UR1, UR2 and the patient couches are in each case fixedly connected to the floor, in other words are arranged in a stationary manner. The couch boards are adjustable with respect to a couch base, in particular in a translational manner, in order to render possible fine positioning of the patient for an imaging and/or an interventional procedure.

The computed tomography system 1 is used to generate tomographic X-ray images both in the first as well as in the second examination space UR1, UR2. The computed tomography system accordingly comprises a gantry G that can be adjusted in a movement direction that extends perpendicular to the gantry G. The movement direction BR extends here along the rail system SS comprising two guide rails. The rails have, as already described in relation to FIG. 1, a length of 12 m. Their length and their extent define the movement radius of the gantry G.

The gantry G is moreover designed as rotatable about a vertical axis VA that extends through the isocenter of the computed tomography system 1. This is rendered possible by the above-described cable routing system KS comprising multiple components, which is likewise included by the CT system 1. In particular, the cable routing system KS comprises a horizontal column HS with 7 m length that is arranged in such a manner that it protrudes above the park position PP and protrudes into the two examination spaces UR1, UR2. In this case, a rotation can be performed in a stationary manner, in other words without parallel translation of the gantry G along the rail system SS or the carriage LW in a parallel direction, simply by adjusting the articulated arms 1G, 2G. Alternatively, the rotation can be performed together with or continuously parallel to a translational movement of the gantry G along the rail system SS.

In FIG. 2, the gantry G stands in the examination space UR2 in the left-hand side maximum position corresponding to the left-hand side end of the rail system SS. The gantry G is rotated in such a manner that it is oriented with its front side toward the outer side (Left-hand side) of the examination space 2. In this position, the patient couch PL2 protrudes with its couch board into the bore of the gantry G. In this position of the gantry G, it is possible to generate tomographic X-ray images of a patient. In order to achieve this position, the cable routing system KS assumes a maximum extended position. The point of articulation 2GP is widened to approximately 170° with the result that the first and second articulated arms 1G, 2G essentially lie one behind the other and their lengths are added. The two articulated arms 1G, 2G do not extend over the gantry G. The carriage LW is likewise located in its left-hand side maximum position in relation to the horizontal column HS. Nevertheless, the third and the first point of articulation 1GP, 3GP are spaced from one another to the maximum extent. The required length of the supply line can be provided via the cable routing system KS until a connection point on the lower end of the vertical column VS.

Figure 3:
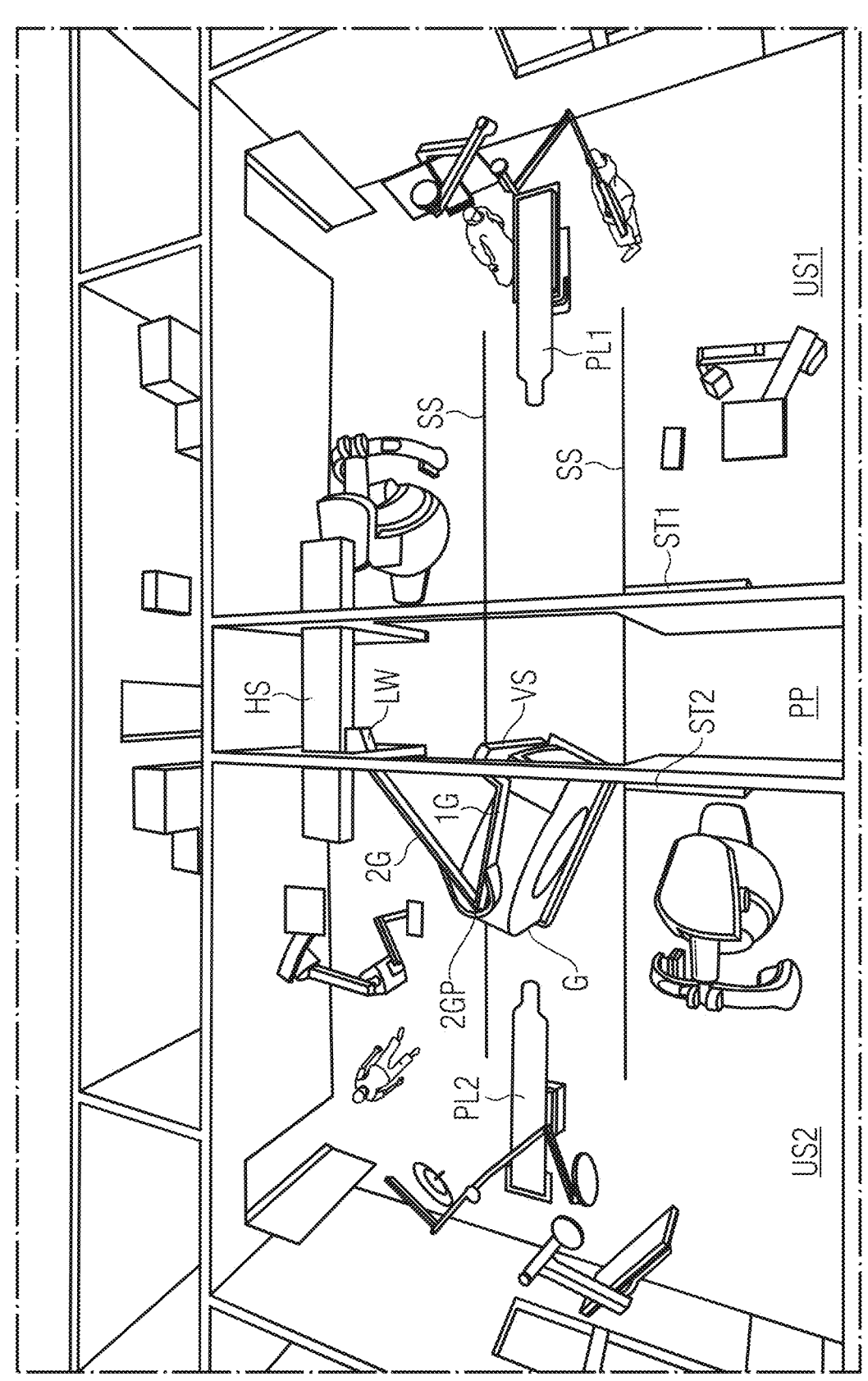
FIG. 3 shows the computed tomography system according to FIG. 2 in a second operating position.
Figure 4:
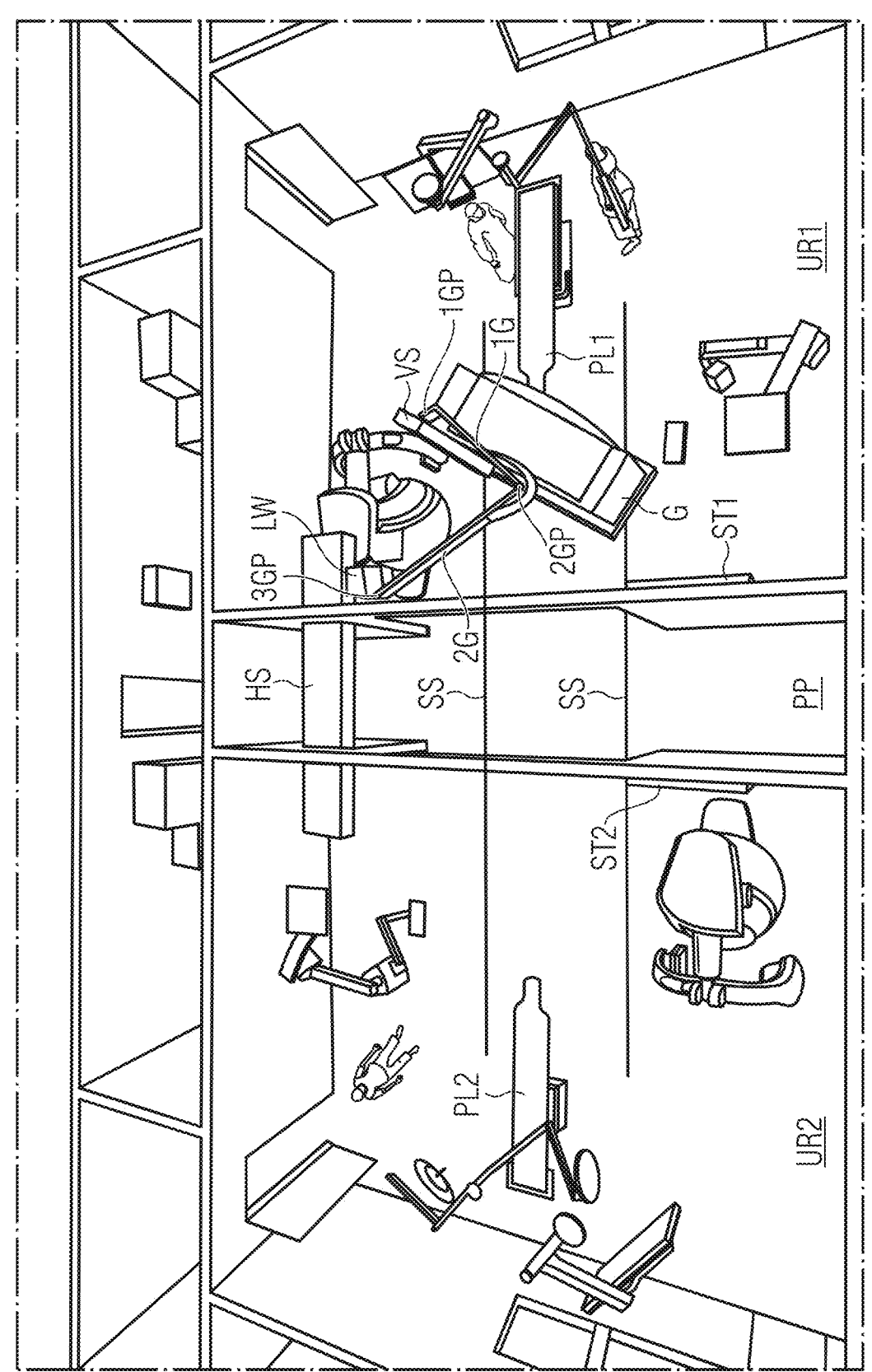
FIG. 4 shows the computed tomography system according to FIG. 2 in a third operating position.
Figure 5:
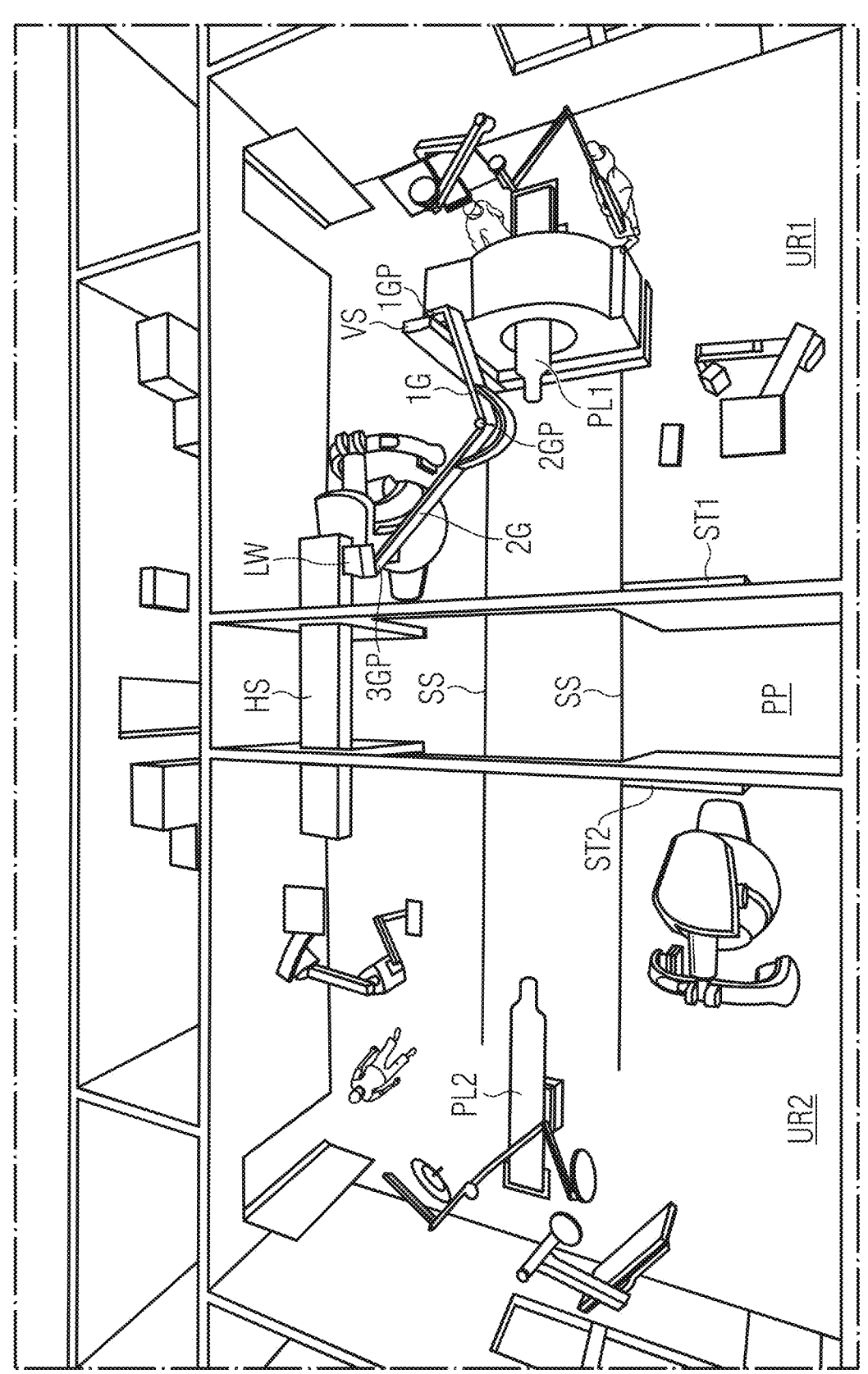
FIG. 5 shows the computed tomography system according to FIG. 2 in a fourth operating position.

FIGS. 3 to 5 illustrate the transition of the gantry G from the left-hand side maximum position into the right-hand side maximum position in the opposite-lying examination space UR1.

FIG. 3 illustrates the computed tomography system 1 corresponding to a second operating position within the examination space UR2. The gantry G is already rotated here by approximately 50° counter-clockwise about the vertical axis VA. The second point of articulation 2GP includes an angle of approximately 45° between the two articulated arms 1G, 2G. The first articulated arm 1G lies here entirely over the gantry G, thus also the second point of articulation 2GP. The carriage LW has assumed a position within the park position PP, in other words has travelled approximately a quarter of its maximum adjustment path along the horizontal column HS.

FIG. 4 illustrates the computed tomography system 1 corresponding to a third operating position within the examination space UR1. The gantry G is already rotated by approximately 150° counter-clockwise about the vertical axis VS. The gantry G has moved itself far into the examination space UR1. The second point of articulation 2GP includes an angle of approximately 80° between the two articulated arms 1G, 2G. The first articulated arm 1G also does not lie here to a large extent over the gantry G, the second point of articulation 2GP and also the second articulated arm 2G. The carriage LW has left the park position PP and likewise moves along the horizontal column HS toward the right-hand side into the examination space UR1. The carriage has travelled approximately four fifths of its maximum adjustment path along the horizontal column HS.

FIG. 5 illustrates the computed tomography system 1 in a fourth operating position in which the gantry G has assumed the right-hand side maximum position in the examination space UR1 corresponding to the right-hand side end of the rail system SS. The gantry G is therefore entirely rotated with respect to FIG. 2 by 180° and the gantry is oriented with its front side toward the outer side (right-hand side) of the examination space UR1. In this position, the patient couch PL1 protrudes with its couch board into the bore of gantry G. In this position of the gantry G, it is possible to again generate tomographic X-ray images of a patient. In particular, the rotation causes the patient couch to be inserted into the floor from outside the room in any examination space and thus awkward adjustment movements with the patient couch can be avoided for the benefit of the patient and to simplify the examination procedure. Moreover, the patient couch PL1, PL2 can be fixedly installed in the examination spaces UR1, UR2. In order to achieve the right-hand side maximum position, the cable routing system KS assumes an extended, if also not maximum extended, position. The point of articulation 2GP is widened to 105° so that the lengths of the first and second articulated arm 1G, 2G are to a large extent added. The two articulated arms 1G, 2G do not extend again over the gantry G. The carriage LW is located in its right-hand side maximum position in relation to the horizontal column HS. The third and the first point of articulation 1GP, 3GP are not spaced to the maximum extent, but are nevertheless spaced particularly wide. In this position of the gantry G, the cable routing system KS can also provide the required length of the supply line until a connection point on the lower end of the vertical column VS.

Figure 6:
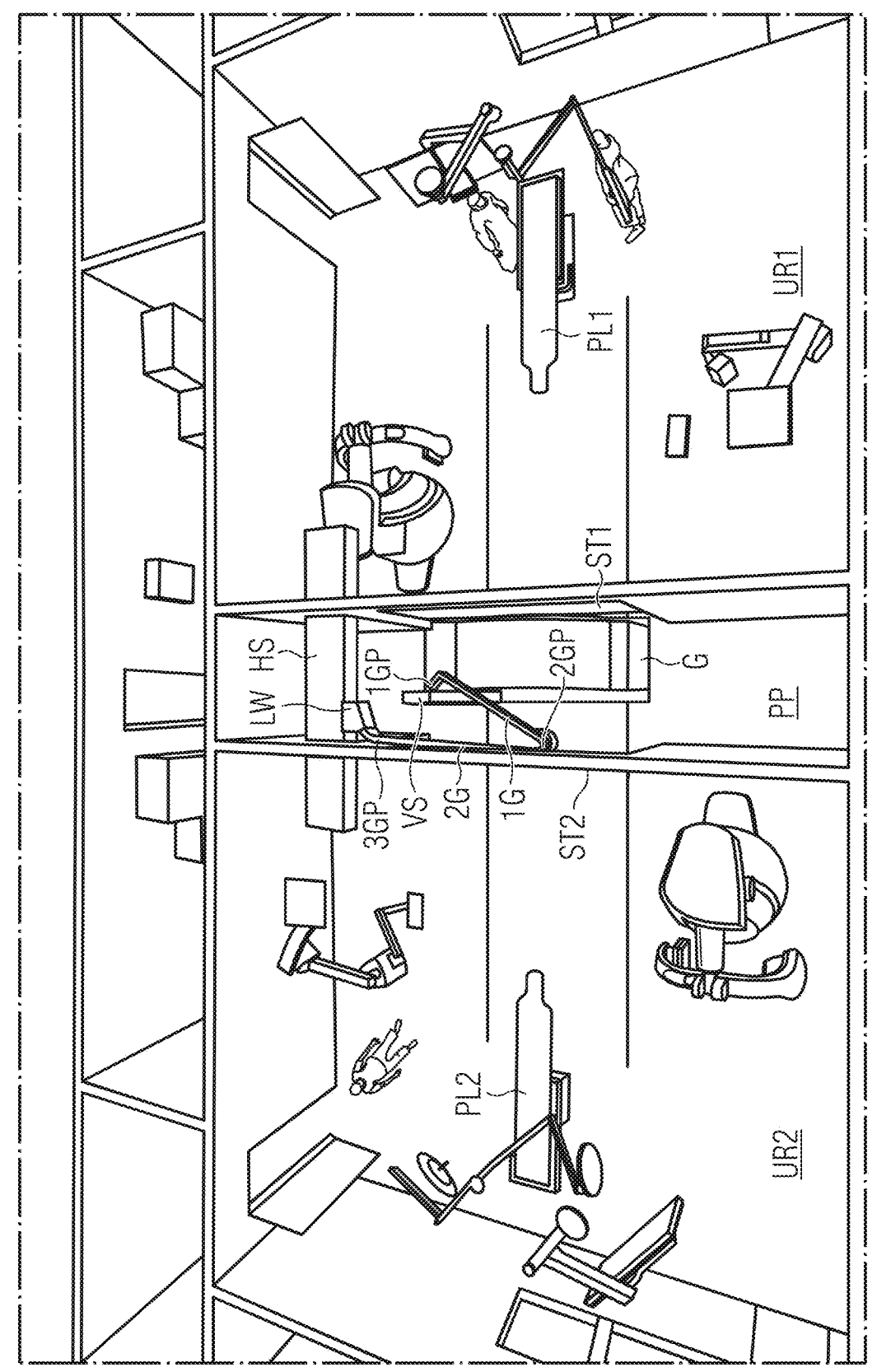
FIG. 6 shows the computed tomography system according to FIG. 2 in a parking position.

FIG. 6 illustrates the computed tomography system 1 according to FIG. 2 in a parking position in which the CT system 1 is not in operation. The CT system 1 here assumes the parking position within the park position PP. During the adjustment movement of the gantry G, opened sliding doors ST1, ST2 of the park position PP can be closed in this case so that each examination space UR1, UR2 can be used differently independent of one another.

The gantry G in the parking position assumes a position that is defined beforehand and that lies to the right-hand side to the maximum extent in the park position PP, wherein the gantry is rotated corresponding to the right-hand side maximum position in such a manner that its front is oriented toward the outer side (right-hand side) of examination space UR1. The second point of articulation GP2 includes here an angle of 10° between the two articulated arms 1G, 2G with the result that these arms are arranged in a space-saving manner essentially adjacent to one another. In particular, the second articulated arm 2G extends in this position essentially parallel to the gantry rear side. In order to achieve this parking position, the carriage LW is actively moved via its drive to the corresponding position along the adjustment path of the carriage on the horizontal column HS in order to achieve the angle of 10° in the second point of articulation 2GP.

Where it is not yet explicitly done but is expedient and in the spirit of the present invention, individual exemplary embodiments, individual of their part aspects or features can be combined with one another or exchanged without departing from the scope of the present invention. With reference to an exemplary embodiment, described advantages of the present invention also relate without explicit mention, where transferable, to other example embodiments.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of the embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing embodiments. The present invention may, however, be embodied in many alternate forms and should not be construed as limited to only the embodiments set forth herein.

What is claimed is:

1. A cable routing system for a computed tomography system, the cable routing system comprising:

a gantry adjustable in a movement direction that extends perpendicular to the gantry;

a vertical column arranged on the gantry and extending vertically upward from a base of the computed tomography system such that the vertical column ends on a floor side of the gantry; and a first articulated arm and a second articulated arm, the first articulated arm being rotatably attached to an upper end of the vertical column above the gantry via a first point of articulation, and being rotatably attached to the second articulated arm via a second point of articulation, the second articulated arm also being arranged above the gantry, wherein the vertical column, the first articulated arm and the second articulated arm are configured to route at least one supply line at least in part along their respective longitudinal axes.

2. The cable routing system for a computed tomography system as claimed in claim 1, wherein the second articulated arm is rotatably attached via a ceiling-mounted third point of articulation above the gantry.

3. The cable routing system for a computed tomography system as claimed in claim 2, wherein the at least one supply line is routed in the vertical column and on at least one of the first point of articulation, the second point of articulation or the ceiling-mounted third point of articulation in a cable carrier.

4. The cable routing system for a computed tomography system as claimed in claim 2, wherein the first articulated arm and the second articulated arm extend in one plane.

5. The cable routing system for a computed tomography system as claimed in claim 2, further comprising:

a horizontal column extending above the gantry and being ceiling-mounted, the horizontal column having a longitudinal axis parallel to the movement direction of the gantry, wherein a carriage is arranged on the horizontal column, the carriage is configured to support the ceiling-mounted third point of articulation, and the carriage is configured to be adjusted in the longitudinal direction of the horizontal column.

6. The cable routing system for a computed tomography system as claimed in claim 5, wherein the at least one supply line is routed at least in part in a cable carrier in the horizontal column.

7. The cable routing system for a computed tomography system as claimed in claim 1, wherein the at least one supply line is routed in the vertical column and on at least one of the first point of articulation, the second point of articulation or a ceiling-mounted third point of articulation in a cable carrier.

8. The cable routing system for a computed tomography system as claimed in claim 1, wherein the first articulated arm and the second articulated arm extend in one plane.

9. The cable routing system for a computed tomography system as claimed in claim 1, wherein the vertical column has an adjustable height, and at least one of the first point of articulation, the second point of articulation or a third point of articulation enable a pivoting movement about a horizontal axis.

10. The cable routing system for a computed tomography system as claimed in claim 1, wherein the second point of articulation is configured such that the first articulated arm and the second articulated arm are configured to be positioned at an angle between 10° and 170°.

11. The cable routing system for a computed tomography system as claimed in claim 1, wherein the first point of articulation is configured such that the first articulated arm and the gantry are configured to be positioned at an angle between 10° and 160°.

12. The cable routing system for a computed tomography system as claimed in claim 1, wherein a length of the first articulated arm corresponds to 65% to 75% of a length of the second articulated arm.

13. The cable routing system for a computed tomography system as claimed in claim 1, wherein the first articulated arm is less than or equal to 1600 mm long and the second articulated arm is less than or equal to 2300 mm long.

14. The cable routing system for a computed tomography system as claimed in claim 1, further comprising:

a horizontal column extending above the gantry and being ceiling-mounted, the horizontal column having a longitudinal axis parallel to the movement direction of the gantry, wherein a carriage is arranged on the horizontal column, the carriage is configured to support a third point of articulation, and the carriage is configured to be adjusted in the longitudinal direction of the horizontal column.

15. The cable routing system for a computed tomography system as claimed in claim 14, wherein the carriage is configured to adjust a height of the third point of articulation.

16. The cable routing system for a computed tomography system as claimed in claim 15, wherein the at least one supply line is routed at least in part in a cable carrier in the horizontal column.

17. The cable routing system for a computed tomography system as claimed in claim 14, wherein the at least one supply line is routed at least in part in a cable carrier in the horizontal column.

18. A computed tomography system for generating tomographic X-ray images, the computed tomography system comprising:

a gantry configured to be adjusted in a movement direction that extends perpendicular to the gantry; and the cable routing system as claimed in claim 1.

19. The computed tomography system for generating tomographic X-ray images as claimed in claim 18, further comprising:

a rail system on which the gantry is configured to be adjusted over a path of less than or equal to 12 m between two examination spaces.

20. The computed tomography system for generating tomographic X-ray images as claimed in claim 19, wherein the gantry is configured to, in case of an adjustment movement along the rail system, rotate by 180° about a vertical axis extending through the isocenter of the gantry.

* * * * *